United States Patent
Adams et al.

(10) Patent No.: US 7,070,591 B2
(45) Date of Patent: Jul. 4, 2006

(54) VASCULAR ACCESS PORT WITH PHYSIOLOGICAL SENSOR

(75) Inventors: H. Clark Adams, Arden Hills, MN (US); Brian P. Brockway, Shoreview, MN (US); Perry A. Mills, Arden Hills, MN (US)

(73) Assignee: Transoma Medical, Inc., St. Paul, MN (US)

( * ) Notice: Subject to any disclaimer, the term of this patent is extended or adjusted under 35 U.S.C. 154(b) by 489 days.

(21) Appl. No.: 10/246,348

(22) Filed: Sep. 17, 2002

(65) Prior Publication Data

US 2004/0054352 A1    Mar. 18, 2004

(51) Int. Cl.
  *A61K 9/22* (2006.01)
  *A61M 31/00* (2006.01)
  *A61M 37/00* (2006.01)

(52) U.S. Cl. ............... 604/891.1; 604/66; 604/288.02; 604/502

(58) Field of Classification Search .. 604/890.1–891.1, 604/288.01–288.04, 65–67, 502; 600/485–488; 607/62
See application file for complete search history.

(56) References Cited

U.S. PATENT DOCUMENTS

| | | | |
|---|---|---|---|
| 4,796,641 A | * | 1/1989 | Mills et al. .................. 600/561 |
| 4,846,191 A | | 7/1989 | Brockway et al. |
| 5,387,192 A | | 2/1995 | Glantz et al. |
| 5,487,760 A | | 1/1996 | Villafana |
| 5,522,394 A | | 6/1996 | Zurbrugg |
| 5,535,752 A | | 7/1996 | Halperin et al. |
| 5,931,829 A | * | 8/1999 | Burbank et al. ............ 604/502 |
| 6,033,366 A | | 3/2000 | Brockway et al. |

(Continued)

FOREIGN PATENT DOCUMENTS

WO    WO 00/16688 A2    3/2000

OTHER PUBLICATIONS

*Clinician Information* PORT-A-CATH® and PORT-A-CATH II® Implantable Venous Access Systems / P.A.S. PORT Implantable Peripheral Venous Access Systems, Smiths Industries Medical Systems, SIMS Deltac, Inc., St. Paul, MN 55112, USA pp. 1-24.

(Continued)

*Primary Examiner*—Catherine S. Williams
(74) *Attorney, Agent, or Firm*—Townsend and Townsend and Crew LLP

(57) ABSTRACT

A combined vascular access port and physiologic parameter monitoring device. The vascular access port and the monitoring device may be connected by a cooperative geometry. The vascular access port and the monitoring device may be implanted at the same time and in the same anatomical location (e.g., subcutaneous pocket). The monitoring device may include a telemetry unit that transmits physiological measurement data to a local data collection system (e.g., carried by the patient or located in the patient's home), which may re-transmit the data to a remote data collection system (e.g., located at a physician's office or clinic) via a suitable communication link.

12 Claims, 11 Drawing Sheets

U.S. PATENT DOCUMENTS

| | | | |
|---|---|---|---|
| 6,122,536 | A | 9/2000 | Sun et al. |
| 6,285,897 | B1 | 9/2001 | Kilcoyne et al. |
| 6,296,615 | B1 | 10/2001 | Brockway et al. |
| 6,527,744 | B1 * | 3/2003 | Kriesel et al. .............. 604/132 |

OTHER PUBLICATIONS

*System Information* PORT-A-CATH® and PORT-A-CATH II® Implantable Venous Access Systems / P.A.S. PORT Implantable Peripheral Venous Access Systems, Smiths Industries Medical Systems, SIMS Deltac, Inc., St. Paul, MN 55112, USA, 12 pages total.

U.S. Appl. No. 10/077,566, filed Feb. 15, 2002, entitled *Devices, Systems and Methods for Endocardial Pressure Measurement* (Our Reference No. 021628-000100US) pp. 1-67.

U.S. Appl. No. 10/246,324, filed Sep. 17, 2002, entitled *Vascular Access Port With Needle Detector* (Our Reference No. 021628-000400US) pp. 1-23.

* cited by examiner

VASCULAR ACCESS PORT WITH PHYSIOLOGICAL SENSOR

BACKGROUND OF THE INVENTION

The present invention generally relates to vascular access ports. In particular, the present invention relates to vascular access ports having associated physiological sensors.

Implantable vascular access ports (VAP) are used extensively in the medical field when recurrent infusions of therapeutic agents into a patient's circulatory system are required over extended periods of time. Such VAPs generally include a housing containing a reservoir and septum, with a catheter extending from the housing. The VAP housing is implanted in a subcutaneous pocket at an accessible location such as the arm, and the catheter extends from the housing to a remote vascular location to provide convenient, repeatable access to the patient's venous or arterial system in the body. In the subcutaneous pocket, the septum of the VAP may be pierced by a needle that is coupled via appropriate tubing to a therapeutic agent source in an intravenous bag or infusion pump, for example, so that the therapeutic agents may be administered. Such a vascular access system may be used in the home or other outpatient settings, as well as inpatient hospital settings.

When infusing therapeutic agents, it is important to monitor certain patient physiological parameters in order to assess if the therapeutic agent is having the desired benefit and/or is causing detrimental side effects. For example, home infusions of antibiotics are often prescribed for patients suffering from aggressive bacterial infections. These infusions are administered for weeks and then terminated if no apparent clinical symptoms exist. In some instances, however, patients remain infected even though no symptoms exist. The residual infection often manifests itself as random temperature spikes lasting for tens of minutes (known as infection rebound or breakthrough) and the patient may or may not be aware of its existence. As such, patient temperature should be monitored because such temperature spikes should signal the attending physician to change antibiotics. As another example, infused inotropic or antihypertensive drugs require patient blood pressure monitoring because of possible hypo or hypertension side effects that may be life threatening.

Conventional options for monitoring temperature include oral, rectal, ear or skin type temperature measurement devices. Blood pressure monitoring typically includes a blood pressure cuff device. In addition to inconvenience, these devices are not desirable due to lack of continuous monitoring and lack of patient compliance in outpatient settings. For example, because temperature spikes only last a brief period of time as discussed above, periodic monitoring may not catch the temperature spike. Furthermore, because these monitoring devices require patient use, and because typical patients do not have professional health care training, the devices are susceptible to incorrect usage, potentially resulting in erroneous measurements.

Thus, there is a need for a monitoring device that is convenient to the patient as well as the physician, provides the potential for continuous monitoring, and reduces patient non-compliance.

BRIEF SUMMARY OF THE INVENTION

To address this need and others, the present invention provides, in one exemplary embodiment, a vascular access port and physiologic parameter (e.g., temperature, blood pressure, etc.) monitoring device that may be inter-connected by a cooperative geometry. The inter-connected vascular access port and monitoring device may be implanted at the same time and in the same anatomical location (e.g., subcutaneous pocket). The monitoring device may include a telemetry unit that transmits physiological measurement data to a local data collection system (e.g., carried by the patient or located in the patient's home), which may re-transmit the data to a remote data collection system (e.g., located at a physician's office or clinic) via a suitable communication link.

Because the combined vascular access port and monitoring device may be implanted at the same time and in the same anatomical location, it is very convenient for the physician and procedurally cost effective. Also, because the monitoring device does not require patient involvement for effective use, it is not as susceptible to patient noncompliance as prior art monitoring devices. In addition, because the monitoring device permits continuous feedback, it is possible to detect patient symptoms that may occur infrequently and for short periods of time. Furthermore, because the monitoring device permits multiple measurements over a long period of time, it is possible to improve accuracy of measurements that lack repeatability by averaging multiple measurements over a period of time.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
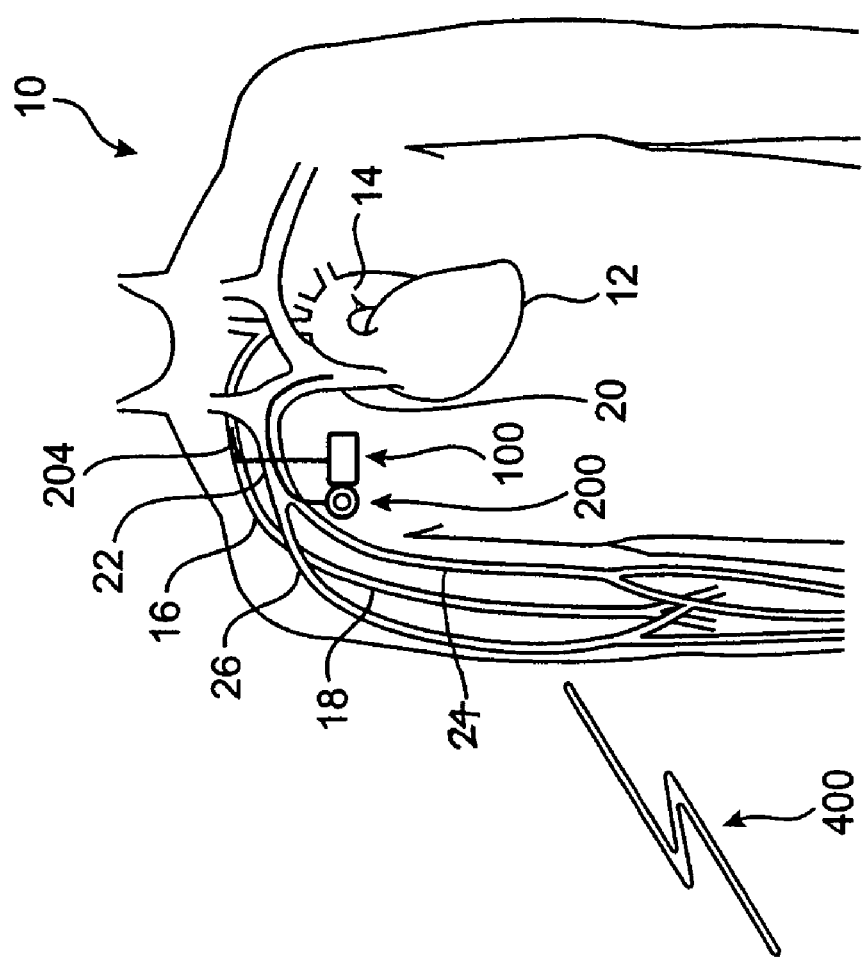
FIG. 1 is a schematic plan view of a vascular access port and physiological monitoring system in accordance with a generic embodiment of the present invention.
Figure 1:
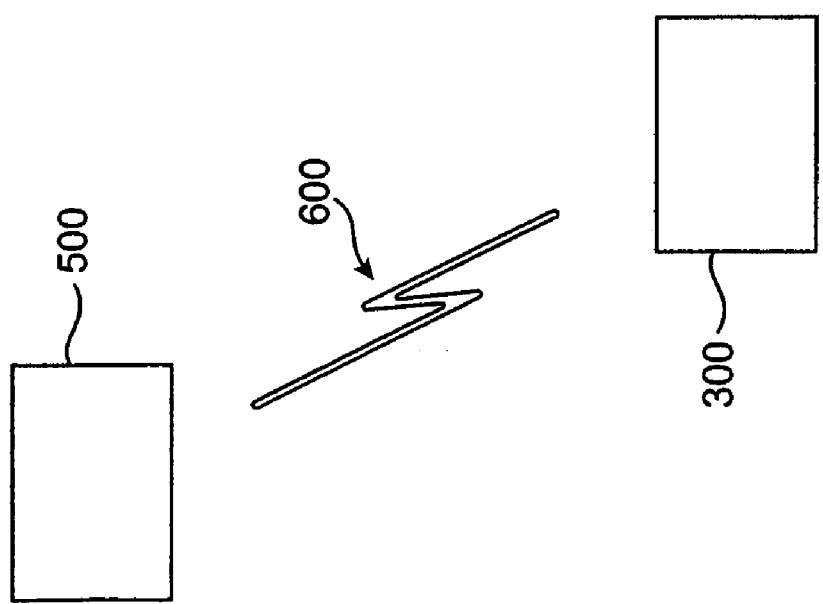

With reference to FIG. 1, a schematic plan view of a generic system including a vascular access port (VAP) 100 and physiological monitoring apparatus (PMA) 200 is shown. The system may be used to deliver therapeutic agents via the VAP 100 while monitoring the patient 10 with the PMA 200. Based on the patient's condition as measured by the PMA 200, the therapeutic regimen (e.g., dose, delivery rate, delivery schedule, etc. of therapeutic agent administered via the VAP 100) may be changed as needed. For example, if the patient 10 adversely reacts to the therapeutic agent delivered via the VAP 100 as measured by the PMA 200, the dose or delivery rate may be decreased or even terminated to reduce or eliminate the adverse effect. Also by way of example, if the patient 10 is not responding to the therapeutic agent delivered via the VAP 100 as measured by the PMA 200, the dose or delivery rate may be increased to establish the desired therapeutic effect. Further by way of example, if the patient 10 demonstrates a need for therapeutic intervention as measured by the PMA 200, the administration of therapeutic agent may be initiated via the VAP 100.

In these and other modes of operation, the PMA 200 provides feedback as to the condition of the patient 10 as indicated by measuring one or more physiological parameters such as blood pressure (arterial, venous, pulse pressure, etc.), temperature, ECG, blood flow velocity, impedance, blood gas levels, blood gas constituents, etc., or combinations thereof. The feedback provided by the PMA 200 may be used to automatically or manually modify the therapeutic regimen (i.e., delivery parameters of the therapeutic agent administered via the VAP 100) as described above. Alternatively, the PMA 200 may provide measurement data indicative of the patient's condition independent of the therapy administered via the VAP 100.

In addition to the VAP 100 and PMA 200, the generic system illustrated in FIG. 1 may include a home (local) data collection system (HDCS) 300 which is operably connected to the PMA 200 via communication link 400, in addition to a physician (remote) data collection system (PDCS) 500 which is operably connected to the HDCS 300 via communication link 600. Communication link 400 may comprise a direct connection (e.g., hardwired transdermal, ohmic, galvanic or body bus) or an indirect (wireless) connection (e.g., radiofrequency, ultrasonic, or infrared transmission). By way of example, not limitation, the communication link 400 may be provided via a conductive needle (not shown) inserted into the VAP 100, wherein the needle is electrically coupled to the HDCS 300 via a wired connection, and electrically coupled to the PMA 200 via a conductive septum, for example. Similarly, communication link 600 may comprise a direct (hardwired) or indirect (wireless) connection, optionally making use of a telecommunication system such as the Internet.

The HDCS 300 may be carried by the patient or may be located in the patient's home, and receives signal data from the PMA 200 via communication link 400. The HDCS 300 may process and store the signal data, and may optionally provide a visual display of the measured parameter and/or an audible alarm indicative of the measured parameter triggering a threshold value. Optionally, the HDCS may obtain an externally derived parameter (e.g., ambient pressure) and associate the external parameter with the signal data from the PMA 200. The data collected and processed by the HDCS 300 may be transferred to the PDCS 500 via communication link 600, which may be located at a physician's office or clinic. The PDCS 500 may further process and store the signal data, and may also provide a visual display of the measured parameter and/or an audible alarm indicative of the measured parameter triggering a threshold value.

Based on information provided by HDCS 300, the patient 10 or the patient's care taker may manually alter the therapeutic regimen as described above. Similarly, based on information provided by PDCS 500, the physician or health care provider may contact (via HDCS 300, for example) and instruct the patient 10 or the patient's care taker to manually alter the therapeutic regimen as described above. Alternatively, if the therapeutic agent is delivered to the VAP 100 by an automated infusion pump or the like, the HDCS 300 may be operably coupled to the infusion pump and may be programmed to modify the delivery parameters as a function of the physiological parameter measured by the PMA 200 and/or as a function of instructions provided by PDCS 500. Further aspects of the function and use of HDCS 300 and PDCS 500 may be found in U.S. patent application Ser. No. 10/077,566, filed Feb. 15, 2002, entitled DEVICES, SYSTEMS AND METHODS FOR ENDOCARDIAL PRESSURE MEASUREMENT, the entire disclosure of which is incorporated herein by reference.

With reference to FIGS. 1, 2A, 2B, and 4, the VAP 100 is shown schematically and may comprise a variety of vascular access port (single or dual port) designs known to those skilled in the art, with certain modification as described in more detail hereinafter. In the illustrated embodiment, the VAP 100 includes a portal housing 102 and an elongate tubular infusion catheter 104 extending therefrom. An internal reservoir 110 (visible in FIG. 4) is contained within the housing 102. The housing 102 includes two openings, both of which are in fluid communication with and provide access to the internal reservoir 110. A side opening in the housing 102 permits passage of the infusion catheter 104 which is in fluid communication with the internal reservoir 110. The side opening in the housing 102 may contain a catheter connector and/or strain relief 108 (visible in FIGS. 2A, 2B and 4). A top opening in the housing 102 contains a self-sealing septum 106 through which a hypodermic or infusion needle may be removably inserted into the internal reservoir 110 for the delivery of therapeutic agents. An example of a suitable VAP 100, with some modification, is disclosed in U.S. Pat. No. 5,387,192 to Glantz et al., the entire disclosure of which is incorporated herein by reference. As an option, the VAP 100 may incorporate a needle detector device as described in U.S. patent application Ser. No. 10/246,324, entitled VASCULAR ACCESS PORT WITH NEEDLE DETECTOR, filed on even date herewith, the entire disclosure of which is hereby incorporated by reference.

With reference to FIGS. 1, 2A, 2B, and 5, the PMA 200 is shown schematically and may comprise a variety of implantable sensor devices known to those skilled in the art, with certain modification as described in more detail hereinafter. Examples of implantable devices that measure blood pressure are described in U.S. Pat. No. 4,846,191 to Brockway et al., U.S. Pat. No. 6,033,366 to Brockway et al., U.S. Pat. No. 6,296,615 to Brockway et al., and PCT Publication WO 00/16686 to Brockway et al., the entire disclosures of which are incorporated herein by reference. Other implantable sensor devices that measure temperature, ECG, blood constituents, etc., may be implemented as well. An example of an implantable device with a temperature sensor is described in U.S. Pat. No. 5,535,752 to Halperin et al., the entire disclosure of which is incorporated herein by reference. An example of an implantable device with temperature, pH and pressure sensing capabilities is disclosed in U.S. Pat. No. 6,285,897 to Kilcoyne et al., the entire disclosure of which is incorporated herein by reference. An example of an implantable device with blood flow velocity measuring capabilities is disclosed in U.S. Pat. No. 5,522,394 to Zurbrugg, the entire disclosure of which is incorporated herein by reference. An example of an implantable device with blood constituent (e.g., blood glucose, blood gas) measuring capabilities is disclosed in U.S. Pat. No. 6,122,536 to Sun et al., the entire disclosure of which is incorporated herein by reference. The sensor components (transducer and pressure transmission catheter) of the PMA 200 may be replaced by the sensor components of the implantable sensor devices described in the patents identified above. In some instances, the transducer may be located on the PMA housing 202, or on a catheter or lead extending therefrom. In other instances, the transducer may be located on the VAP housing 102 or the catheter 104 extending therefrom.

For purposes of illustration, the present invention is described herein primarily with reference to embodiments utilizing a PMA 200 that measures blood pressure as described in Brockway et al. '191. To this end, in the embodiment illustrated in FIGS. 1, 2A, 2B, and 5, the PMA 200 comprises a blood pressure measuring device including a sensor housing 202 with a pressure transmission catheter (PTC) 204 extending therefrom. The PMA 200 also includes a pressure transducer and electronics module 210, a telemetry unit 220 and a power supply 230 (e.g., battery, external power source with transdermal connection, etc.) contained in housing 202 (visible in FIG. 5).

The housing 202 protects the pressure transducer and the electronics module 210, the telemetry unit 220, and the power supply 230 from the harsh environment of the human body. The housing 202 may be fabricated of a suitable biocompatible material such as titanium or ceramic and may be hermetically sealed. If metallic, the outer surface of the housing 202 may serve as an electrocardiogram (ECG) sensing electrode. The housing may include one or more rings (not shown) and/or a mesh fabric (not shown) disposed thereon for attachment to bodily tissue in the subcutaneous pocket.

The PTC 204 refers pressure from the pressure measurement site to the pressure transducer and electronics module 210 located inside the sensor housing 202. The PTC 204 may comprise a tubular structure with a liquid-filled lumen extending therethrough to a distal opening or port. The proximal end of the PTC 204 is connected to the pressure transducer via a nipple tube, thus establishing a fluid path from the pressure transducer to the distal end of the PTC 204. A barrier such as a viscous or movable plug and/or membrane may be disposed in the distal opening of the PTC 204 to isolate the liquid-filled lumen of the PTC 204 from bodily fluids, without impeding pressure transmission therethrough.

As an alternative, the PTC 204 of the PMA 200 and the infusion catheter 104 of the VAP 100 may be combined into one dual lumen tube, wherein the PMA 200 measures blood pressure and the VAP 100 delivers therapeutic agent in the same blood vessel. As another alternative, the PTC 204 the infusion catheter 104 may be combined into a single lumen tube, wherein a valve is used to alternatively provide fluid communication between the PMA 200 and the single lumen catheter to measure blood pressure, and provide fluid communication between the VAP 100 and the single lumen catheter to deliver therapeutic agent. In addition or in the alternative, the PMA 200 may be used to measure fluid flow and/or pressure in the VAP 100 during infusion, in addition to measuring a physiological parameter.

The pressure transducer and electronics module 210 may be the same or similar to those described in U.S. Pat. Nos. 4,846,191, 6,033,366, 6,296,615 or PCT Publication WO 00/16686, all to Brockway et al. The electronics module provides excitation to the pressure transducer, amplifies the pressure signal, and may digitally code the pressure information for communication to the telemetry unit 220. The electronics module may also provide for temperature compensation of the pressure transducer and provide a calibrated pressure signal.

The telemetry unit 220 includes telemetry electronics, which may be the same or similar to those described in U.S. Pat. Nos. 4,846,191, 6,033,366, 6,296,615 or PCT Publication WO 00/16686, all to Brockway et al. The telemetry unit 220, receives a physiological parameter (e.g., pressure) signal from the pressure transducer and electronics module 210, and transmits the data signal to the HDCS 300 via communication link 400. In addition or in the alternative, the telemetry unit 220 may include memory interrogatable by the HDCS 300. Communication link 400 may comprise a direct connection (e.g., hardwired transdermal, ohmic, galvanic or body bus) or an indirect (wireless) connection (e.g., radiofrequency, ultrasonic, or infrared transmission). For wireless RF transmission, a telemetry coil or antenna may be provided in the housing 202, or an antenna may be provided in the PTC 204 as described in more detail hereinafter.

The pressure as measured by the PMA 200 is influenced by external pressure changes (i.e., barometric pressure) and is preferably corrected to avoid inaccuracies and/or possible misinterpretation of pressure data. Barometric pressure can change significantly when a weather front moves through the area where the patient resides, when the patient is riding up an elevator in a tall building or traveling in mountainous areas where changes in elevation are frequent and significant. Thus, the present invention provides a number of different pressure correction schemes as described herein.

One general approach is to take barometric pressure measurements simultaneously with measurements taken by the PMA 200, and subtract the barometric reading from the internal pressure measurement. For example, the HDCS 300 may take a barometric pressure reading and subtract the barometric pressure measurement from the pressure measurement transmitted by telemetry unit 220 of the PMA 200.

For example, a barometric pressure monitor (BPM) may be located external to the body and measure barometric pressure at times specified by a controller. Measurements obtained by the BPM are representative of the barometric pressure to which the body of the patient is exposed. The BPM may be a small device attached to a belt, worn on the neck as a pendant, on the wrist like a watch, or placed in a purse or briefcase. The BPM may be incorporated into the HDCS 300, for example.

At some time, e.g. the first measurement obtained after the BPM is powered on, the absolute value of barometric pressure is stored in the memory of a computing device, which may be incorporated into the BPM, for example. The absolute value of barometric pressure is stored in the memory along with a time stamp (e.g. year, month, day, hour, minute and second). From then on, each subsequent barometric pressure measurement is compared to the stored measurement and evaluated to determine if the difference between that measurement and the stored measurement exceeds a predetermined threshold (e.g. 0.5 mmHg). If the difference is less than the threshold, no further action is taken on that measurement. If the difference is greater than or equal to the threshold, then that value is saved in memory along with a time stamp. If a chronic time series is collected from the patient, the memory of the computing device in the BPM contains barometric pressure values at each point in time where the pressure changed significantly (significant as determined by the preset value).

With this approach, pressure measurements taken by the PMA 200 are made with respect to a specific reference pressure, normally to a vacuum. Pressure measurements are recorded into memory in the PMA 200. Measurements are stored in a way that allows the date and time of the recording to be established. At various times, the pressure measurements recorded in the PMA 200 are transferred to an external combining device (CD) through means of a wireless link. The CD may also be incorporated into the HDCS 300, for example, and the BPM also has the ability to transfer measurements to the CD. This transfer can be made through a hard link (e.g., electrically conductive wires or fiber optics) if the BPM and CD are in the same unit such as HDCS 300, or via a wireless link (e.g., RF transmission) if the BPM and CD are remote from each other. Once data from both the PMA 200 and the BPM are transferred to the CD, the CD can correct the measurements obtained from the PMA 200 for barometric pressure. Knowing the barometric pressure measurements at the starting time and at each point thereafter when pressure changes by a significant amount, it is possible to know the barometric pressure at any time up until the date and time of the last value recorded in memory. Correction of a measurement from the PMA 200 for barometric pressure can be achieved by subtracting the barometric pressure measurement reconstructed at that time point, or by mathematically manipulating the two time series to achieve a result equivalent to subtraction.

A variation of this approach is to record corrected measurements within the PMA 200. In some cases it is useful to have the corrected pressure measurements available within the PMA 200, such as when the PMA 200 is in communication with a device that is providing therapeutic effect, such as an infusion pump, pacemaker or defibrillator, and is relying on accurate pressure measurements to adjust the therapy parameters. Such a therapeutic device may be implanted or external (e.g., a drug infusion pump or wearable defibrillator).

The BPM may transmit barometric pressure data to the PMA 200, which subtracts the barometric measurement from the in vivo pressure measurement and utilizes or otherwise stores the corrected measurement. Alternatively, the in vivo pressure measurements may be transmitted to the BPM which corrects the pressure measurement from the PMA 200 for barometric pressure and transmits the corrected pressure measurement back into the PMA 200.

Alternately, the BPM may evaluate the barometric pressure measurements as they are obtained. In this alternative embodiment, the BPM would transmit the barometric pressure to the PMA 200 when it is first turned on or brought into the receiving range of the BPM. Once this initial measurement is received by the PMA 200, if a measurement differs from the previous value by more than a predetermined threshold, then (and only then) would the BPM transmit a barometric pressure measurement to the PMA 200. The PMA 200 would then send a confirming transmission to the BPM indicating that the transmission of barometric pressure was correctly received. The BPM may continue to send the measurement at regular internals until such confirmation is received.

Another general approach is to provide a reference pressure for the PMA 200. For example, a barometric reference pressure may be provided via a needle inserted into a reference septum in the PMA 200 as described with reference to FIGS. 6 and 7. Alternatively, a barometric reference pressure may be provided via a needle inserted into the septum of the VAP 100, which is in fluid communication with the PMA 200 as described with reference to FIG. 2A.

With reference back to FIG. 1, the VAP 100 is shown implanted with the housing 102 in a subcutaneous pocket and the catheter 104 inserted in a vein. Similarly, the PMA 200 is shown connected to and adjacent the VAP 100 in the same subcutaneous pocket, with the PTC 204 disposed in an artery. Those skilled in the art will recognize that the VAP 100 may be implanted in a variety of subcutaneous locations, and that the infusion catheter 104 may be inserted at a variety of venous locations with varying access and terminus sites. Similarly, those skilled in the art will recognize that PMA 200 may be implanted in a variety of subcutaneous locations, and that the PTC 204 may be inserted at a variety of vascular lumens, organ cavities, interstitial spaces etc., depending on the type of sensor utilized and the type of physiological parameter measured. In addition, because some types of sensors do not require a PTC 204, the PMA 200 may exclude the PTC 204 and simply be implanted adjacent the VAP 100.

In the specific implant example shown in FIG. 1, the infusion catheter 104 of the VAP 100 may be disposed in the basilic vein 24 or cephalic vein 26 which converge into the auxiliary vein 22. The infusion catheter 104 may extend through the auxiliary vein 22 and the superior vena cava 20, and into the right atrium or right ventricle of the heart 12. The PTC 204 of the PMA 200 may be disposed in the brachial artery 18 which communicates with the left ventricle of the heart 12 via aortic arch 14 and subclavian artery 16. Although the patient 10 in this example is shown as a human, the present invention is equally applicable to other animals as well.

Figure 2A:
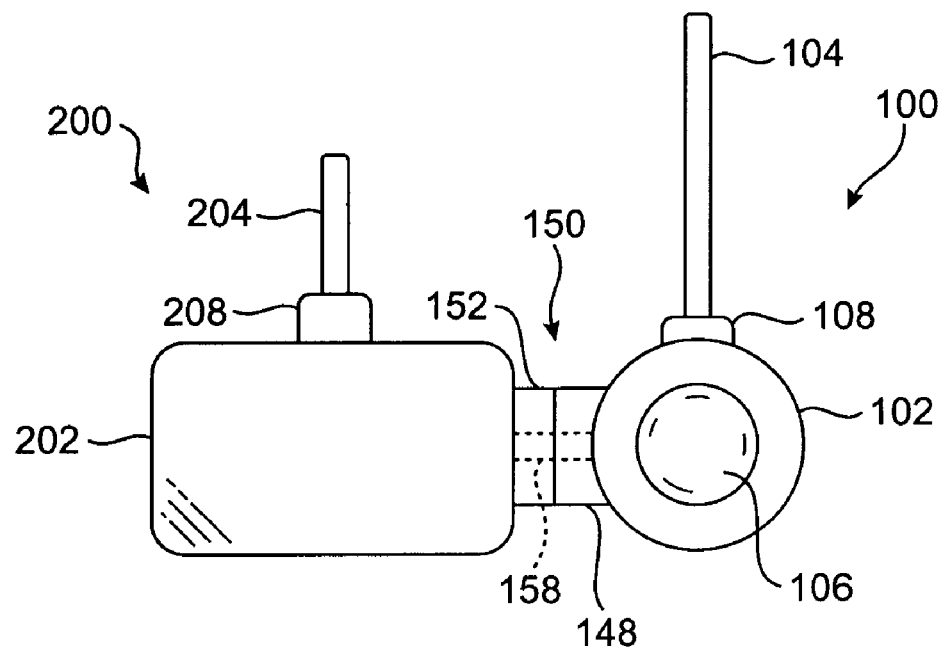
FIG. 2A is a schematic view of a vascular access port and physiological monitoring apparatus connected together by a connector element.
Figure 2B:
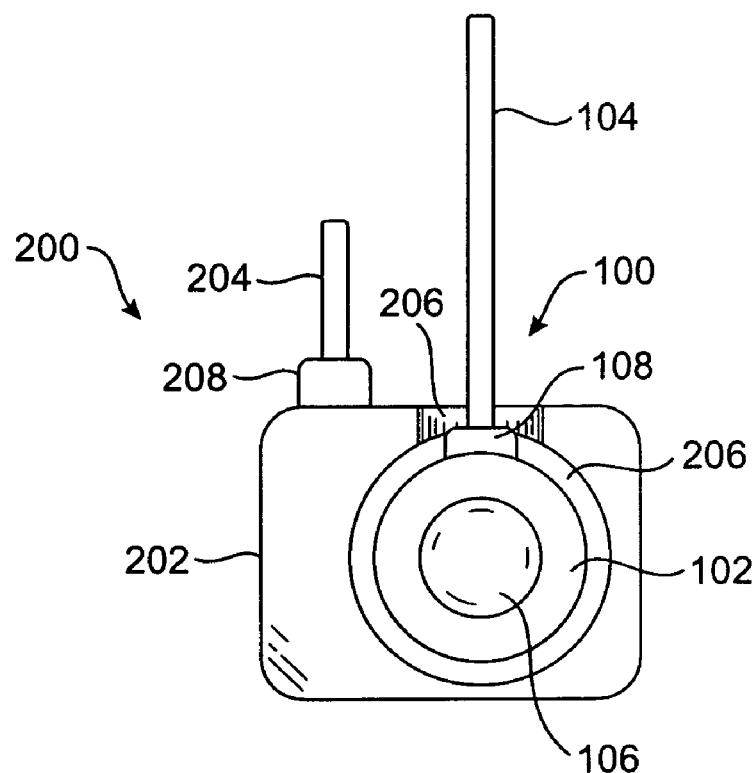
FIG. 2B is a schematic view of a vascular access port and physiological monitoring apparatus connected together by a cooperative geometry.
Figure 4:
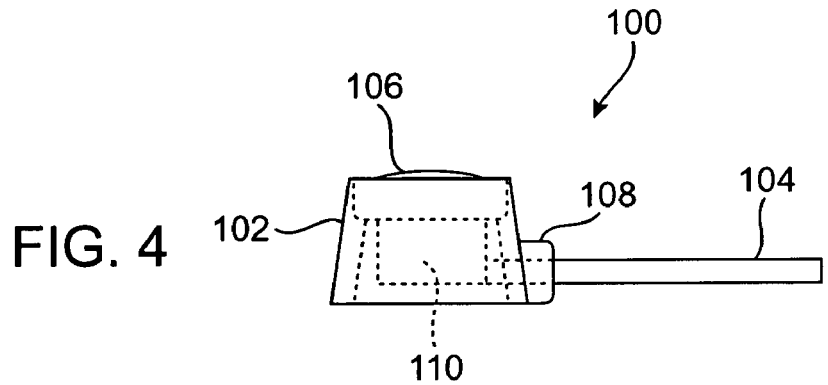
FIG. 4 is a schematic illustration of a vascular access port for use in the present invention.
Figure 5:
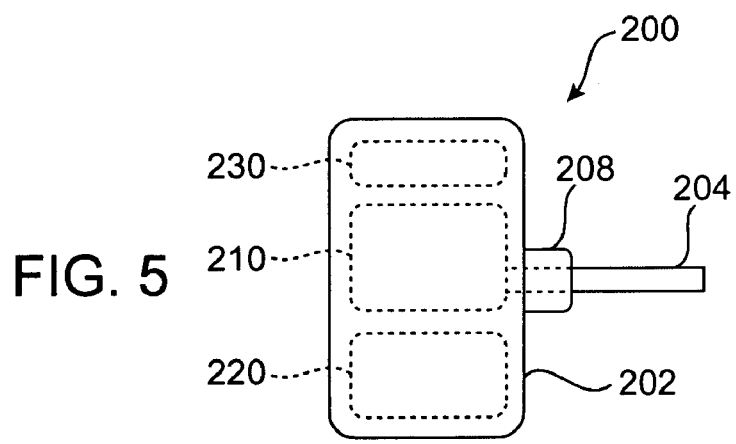
FIG. 5 is a schematic illustration of a physiological monitoring apparatus for use in the present invention.

With reference to FIGS. 2A and 2B, the VAP 100 and PMA 200 are connected together by a cooperative connector geometry and a cooperative housing geometry, respectively. In FIG. 2A, the cooperative geometry is defined external of the port housing 102 and sensor housing 202. In FIG. 2B, the cooperative geometry is defined internally by one of the VAP 100 and PMA 200, and externally by the other. As used herein, the term cooperative geometry or geometries refers to geometries that limit relative movement along two or more orthogonal directions or axes. For example, mating geometries and interlocking geometries, whether fixed together or separable, comprises cooperative geometries.

With specific reference to FIG. 2A, the connector element 150 includes a port portion 148 and a sensor portion 152, each of which define geometries that are cooperative. The port portion 148 of the connector element 150 may be connected to the port housing 102, and may be a separate or an integral component. Similarly, the sensor portion 152 of the connector element 150 may be connected to the sensor housing 202, and may be a separate or an integral component.

Figure 3A:
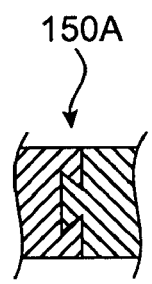
FIGS. 3A–3D are schematic illustrations of various connector element designs for use in the vascular access port and physiological monitoring apparatus illustrated in FIG. 2A.
Figure 3B:
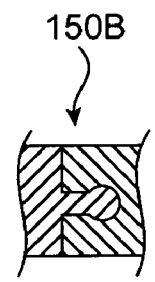
Figure 3C:
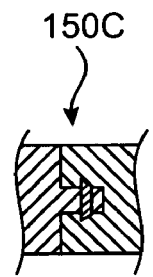
Figure 3D:
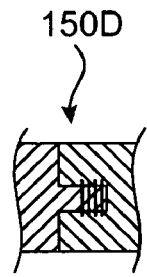

Examples of such connector elements 150 with cooperative geometries are shown in FIGS. 3A–3D. In FIG. 3A, the connector element 150A defines a dove-tail interlocking geometry. In FIG. 3B, the connector element 150B defines a ball-and-socket interlocking geometry. In FIG. 3C, the connector element 150C defines a snap-fit (tapered ridge in groove) geometry. In FIG. 3D, the connector element 150D comprises a threaded shaft and bore geometry.

Connector element 150 may optionally incorporate a lumen 158 through which a fluid path may be established between the VAP 100 and the PMA 200. The lumen 158 may be used, for example, for measuring the pressure or flow rate of fluid infused through VAP 100 utilizing PMA 200, for providing a reference pressure to the PMA 200 via a secondary port in the VAP 100, or for utilizing a common catheter for infusion and pressure measurement.

With specific reference to FIG. 2B, the port housing 102 and the sensor housing 202 define cooperative geometries. As shown, the VAP 100 defines an external geometry which cooperates with an internal geometry of the PMA 200. It is also possible to have the PMA 200 define an external geometry which cooperates with an internal geometry of the VAP 100. In the illustrated embodiment, the PMA 200 defines a cylindrical hole or recess 206 which accommodates the cylindrical housing 102 of the VAP 100, in addition to the infusion catheter 104 and the catheter connector/strain relief 108.

FIGS. 1–5 and the corresponding text schematically illustrate and describe generic embodiments of the present invention. Reference may be made to FIGS. 6–13 for detailed embodiments that incorporate the general principles discussed above.

Figure 6:
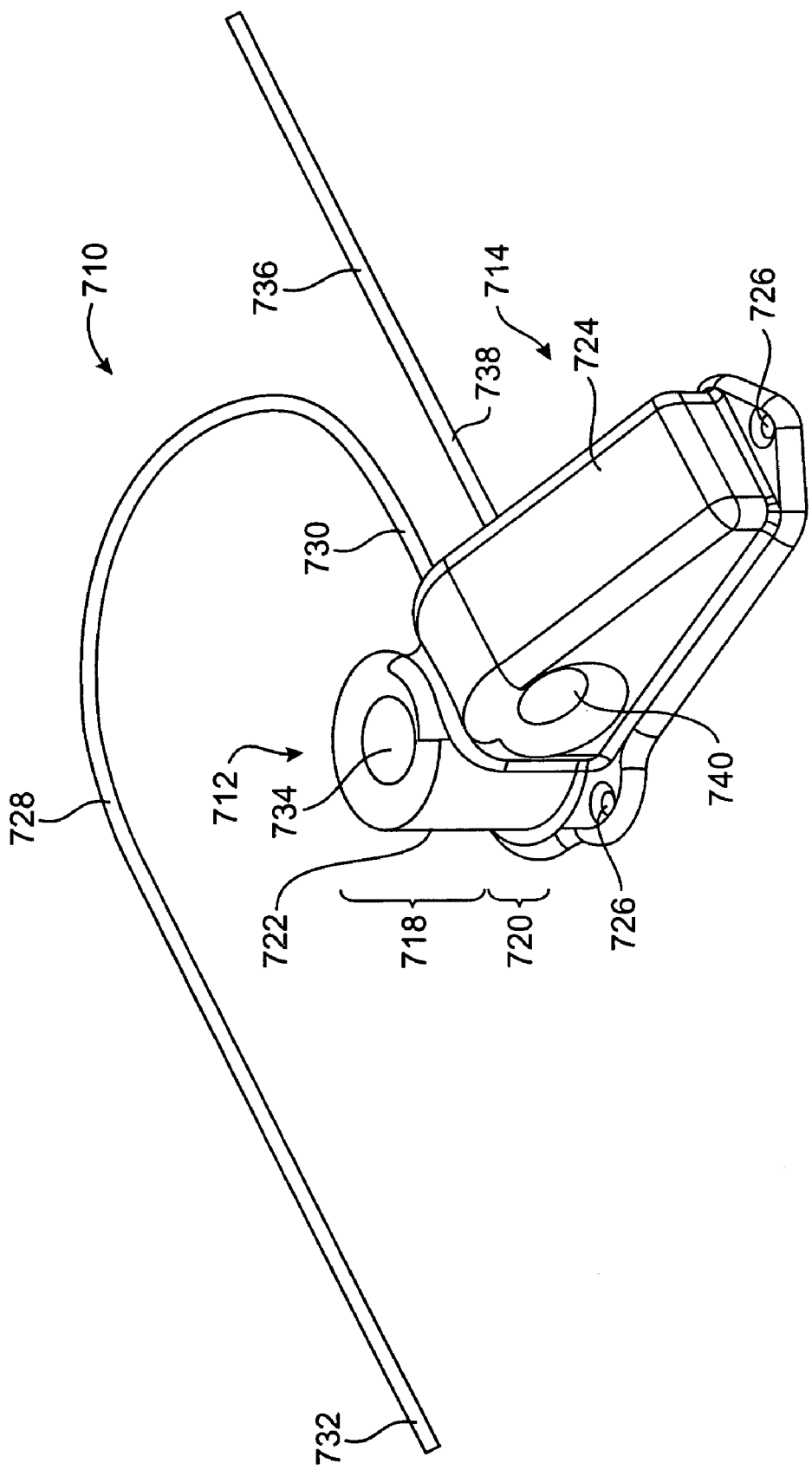
FIG. 6 is a perspective view of a vascular access port and physiological monitoring apparatus in accordance with a specific embodiment of the present invention.
Figure 7:
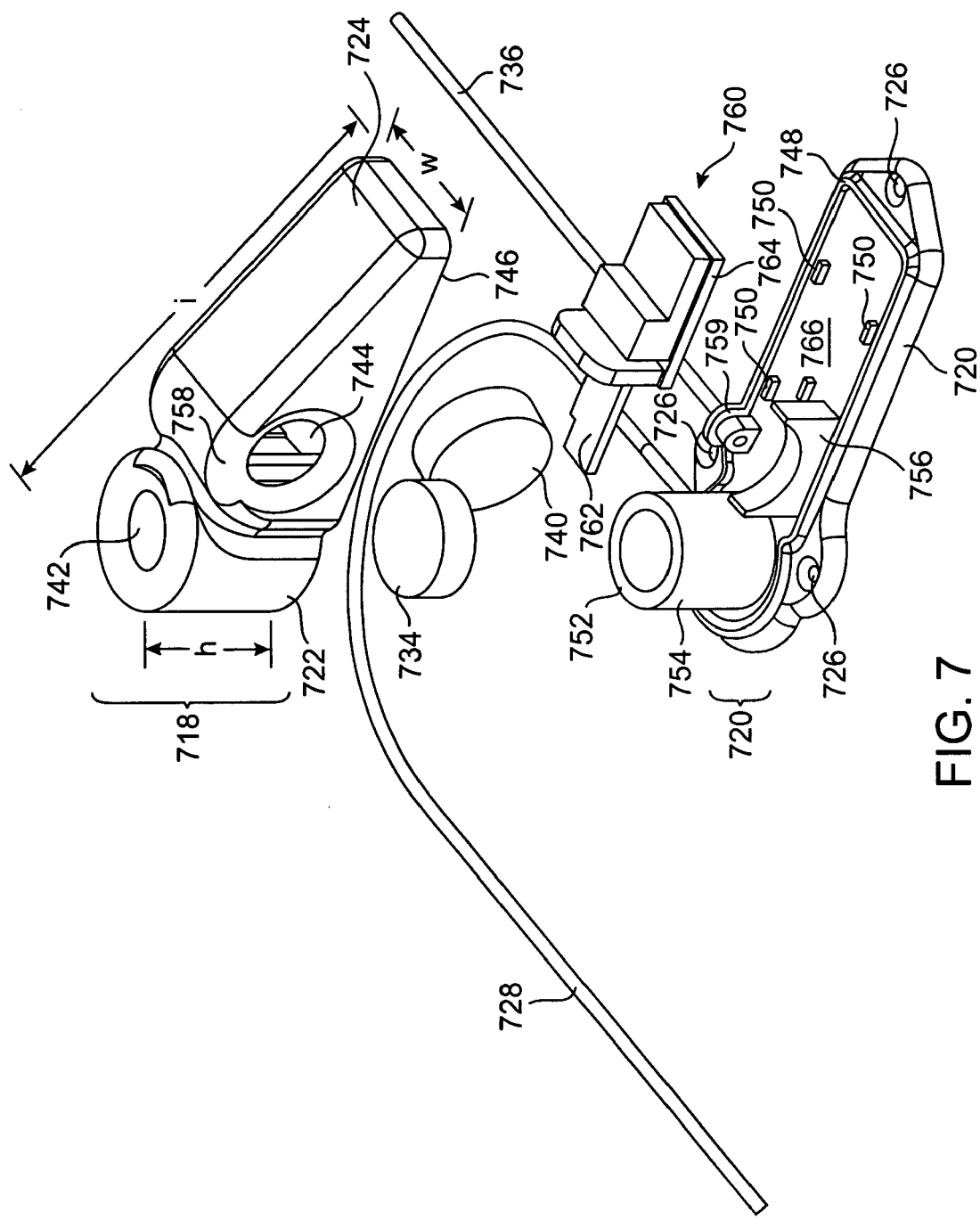
FIG. 7 is an exploded perspective view of the vascular access port and physiological monitoring apparatus illustrated in FIG. 6.

With specific reference to FIG. 6, a combined vascular access port and physiological monitoring apparatus is shown generally as 710. The system 710 includes a vascular access port (VAP) 712 and physiological monitoring apparatus (PMA) 714. An exploded view of the combined VAP and PMA 710 is shown in FIG. 7.

A housing, comprising a mating cap 718 and base 720 pair, contains the internal components of both the VAP 712 and PMA 714. In this embodiment, the cap 718 is an integrally formed component that includes the side-by-side, generally cylindrical vascular access port portion 722 and the generally triangular-solid shaped PMA portion 724. A plurality of suture holes 726 are provided in the base 720 for securing the housing 718/720 to bodily tissue during surgical implantation thereof.

The VAP 712 includes an infusion catheter 728 that extends from the VAP housing 722. A proximal end 730 of the infusion catheter 728 is connected to and is in fluid communication with a reservoir 754, and a distal end 732 of the catheter 728 is disposed in the patient's vascular system. The therapeutic agent is delivered to the infusion catheter 728 via a needle (not shown), coupled via appropriate tubing to a therapeutic agent source in an intravenous bag or infusion pump, for example, that penetrates the infusion septum 734 and communicates with reservoir 754.

The PMA 714 includes a pressure transmission catheter (PTC) 736 coupled at its proximal end 738 to the pressure transducer and electronics package 760 for measuring an internal body pressure. Such pressure might include, but is not limited to, arterial pressure, venous pressure, cardiac chamber pressure, intracranial pressure, intrauterine pressure, bladder pressure, or intrapleural pressure. The PTC 736 may comprise the type described in Brockway '191 or the type described in Brockway '366, for example. A pressure reference septum 740 is provided that is penetrable by a needle (not shown) for providing a reference pressure, such as atmospheric pressure.

In this manner, a combined VAP and PMA 710 is disclosed that allows the combined convenience of a VAP and the simultaneous ability to monitor a physiological parameter of a patient without requiring a practitioner to independently monitor the parameter. It also allows this to be accomplished in a single surgical procedure which presents virtually no additional surgical effort on behalf of the surgeon who would otherwise have implanted a VAP. It adds virtually no additional procedure time or expense either.

Although various geometries are possible, the cap 718 may be generally about 25 mm in length (l), about 12 mm in width (w), and about 15 mm in height (h). The cap 718 may be formed of a titanium, titanium-plastic combination or a titanium-ceramic combination. Two access ports (holes) in the cap 718, infusion septum access port 742 and pressure reference septum access port 744, provide needle access during use to the infusion septum 734 and pressure reference septum 740, respectively. In one embodiment, the septa are formed of a silicone elastomeric material. The septa are mechanically secured when the cap 718 is mated to the base 720.

In the embodiment shown, the cap 718 mates with the base 720 by pinching an edge 746 of the cap 718 between a wall periphery 748 of the base 720 and a plurality of tabs 750. The distance of the tabs 750 from the wall periphery 748 may be selected relative to the thickness of the edge 746 of the cap 718 to form a snug interference fit. The cap 718 and the base 720 may further be adhesively bonded and sealed with a suitable biocompatible adhesive.

When mated, the infusion septum 734 overlays a top 752 of the fluid reservoir 754. In this manner, a needle may penetrate the infusion septum 734 and deliver a therapeutic agent to the fluid reservoir 754. In turn, the therapeutic agent is delivered to the patient via the infusion catheter 728 which is in fluid communication with the fluid reservoir 754.

The pressure reference septum 740 is secured between a clamshell structure 756 of the base 720 and a curved portion 758 of the cap. In this manner, it will be appreciated that atmospheric pressure (reference pressure) may be provided via a needle penetrating the pressure reference septum 740 of the PMA 714, which avoids the use of elaborate barometric pressure reference devices when measuring arterial or venous pressure.

The PTC 736 is connected to the base 720 via a retaining mechanism 759. The pressure transducer and electronics package 760, powered by battery source 762, is coupled to the PTC 736. A substrate 764 may support the electronics package 760 and rest on the floor 766 of the base 720 housing.

Figure 8:
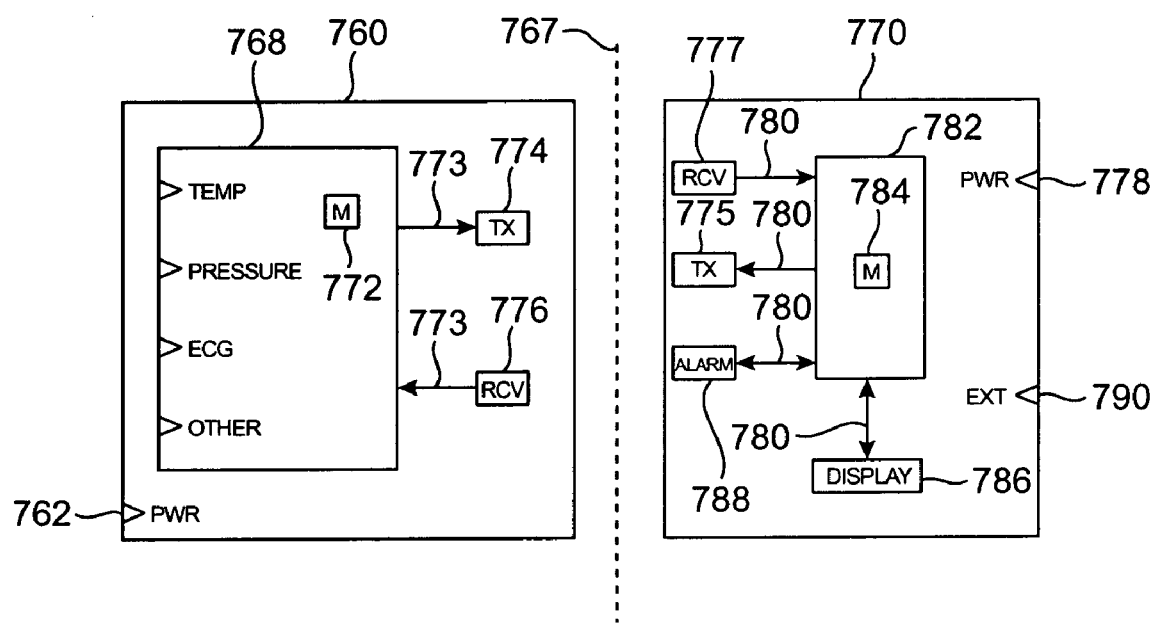
FIG. 8 is a block diagram of the electronics of a physiological monitoring apparatus and associated transceiver for use with the embodiment illustrated in FIG. 6.
Figure 9B:
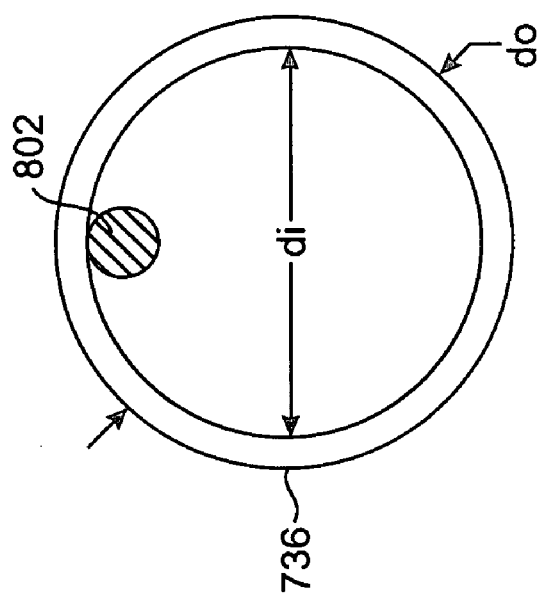
FIG. 9B is an end view of the pressure transmission catheter and antenna illustrated in FIG. 9A.
Figure 9A:
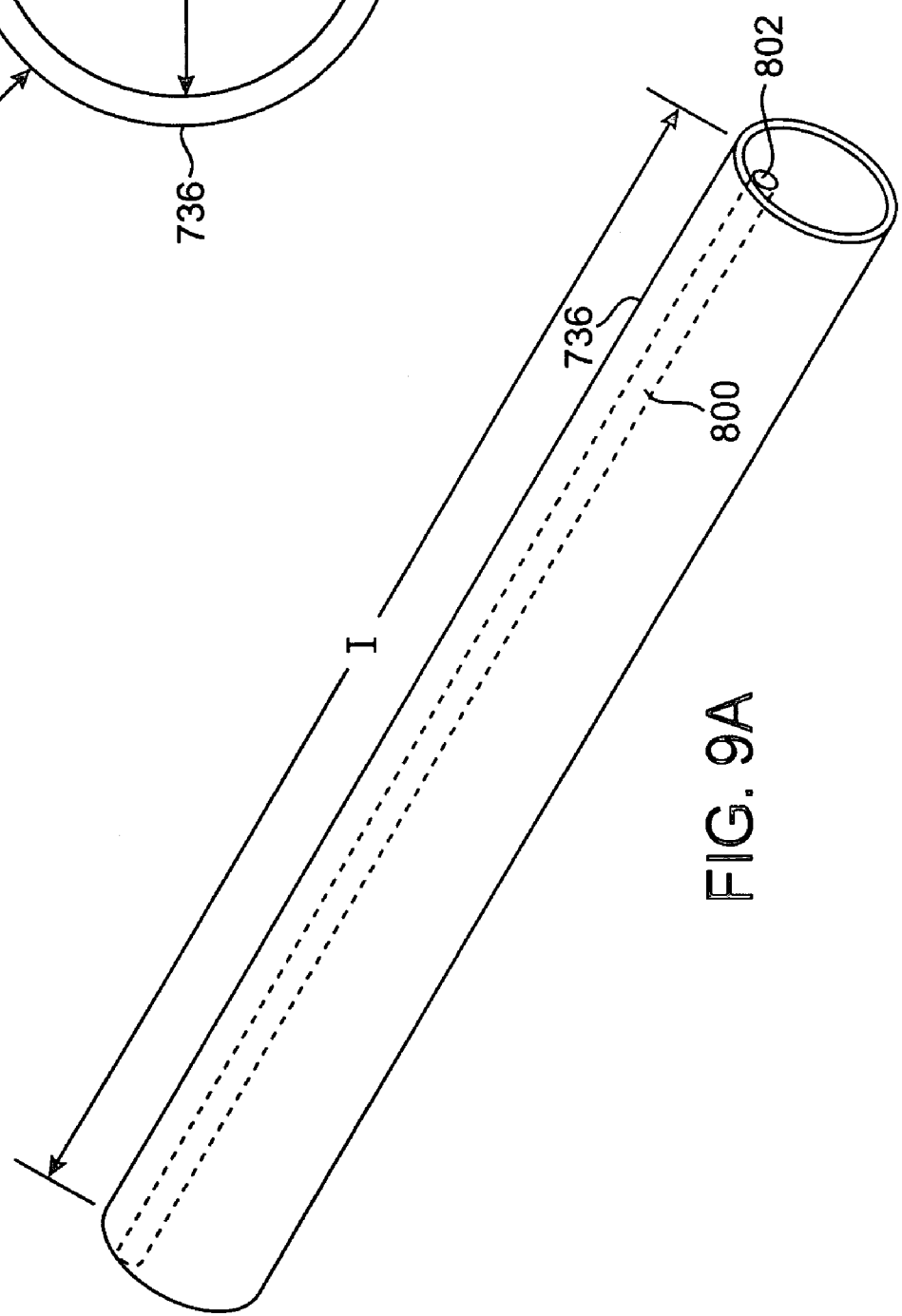
FIG. 9A is a perspective view of a pressure transmission catheter having an antenna for use with the physiological monitoring apparatus illustrated in FIG. 6.

With reference to FIG. 8, the pressure transducer and electronics module 760 of the PMA 714 may be implanted within a patient's body (shown as being to the left side of a dashed line 767 representing the skin surface of the patient)

and communicates, regarding measured physiological parameters, with a transceiver 770 external to the patient's body (shown as being to the right side of the dashed line 767).

The pressure transducer and electronics module 760 may comprise a processor 768 having a memory 772 for permanent or temporary storage of various algorithms, routines, computer executable instructions, and/or storage of the measured physiological parameter. The memory may be any well known random-access or read-only type memory, or both. A temperature input (Temp), a body pressure input (Pressure), an electrocardiogram electrode input (ECG) or other input desired to be measured by the PMA are supplied to the processor 768 via appropriate electronic communications paths. Other inputs include, but are not limited to, blood flow, blood glucose, blood gas (e.g., oxygen saturation, CO2).

Figure 13:
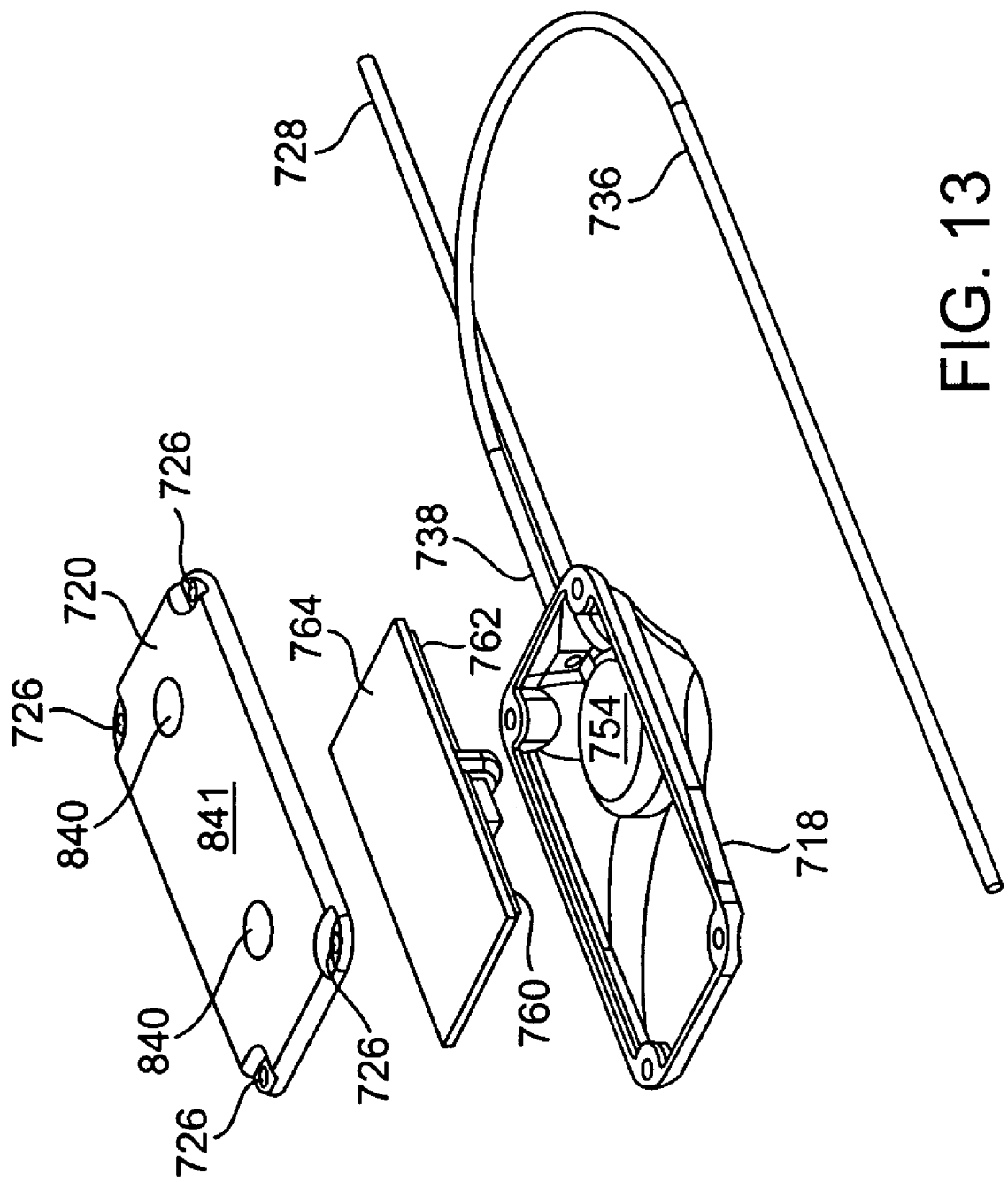
FIG. 13 is an exploded perspective view of another alternative embodiment of a vascular access port and physiological monitoring apparatus connected together by a common or integral housing.

The body pressure input may be provided via the PTC 736 and pressure transducer in module 760 as described with reference to FIGS. 6 and 7. The temperature input may be received from a thermistor (not shown) mounted internally or externally to the housing 718/720. A benefit of locating the thermistor externally to the housing is to minimize temperature error induced by the therapeutic agent flowing through the VAP and to obtain temperature at a very specific body location. The ECG input may be received from a ECG electrodes mounted on the housing 718/720, the PTC 736, and/or the infusion catheter 728. For example, ECG electrodes 840 may mounted on a bottom surface 841 of base 720 as shown in FIG. 13.

The electronics package and battery source may be hermetically sealed to prevent the electronics from electrically shorting or corroding as a result of water vapor penetration. The battery source 762 (rechargeable and/or replaceable) provides the power input (Pwr) to the electronics package. It may comprise a physical battery or a capacitor, for example, and may be implanted with the device or located external to the body and wirelessly coupled to the electronics package by utilizing a magnetic coupling, for example. Such a magnetic coupling may utilize an AC powered primary (external) coil disposed on the skin to create an alternating magnetic field which induces power in a secondary (internal) coil connected to the electronics package and disposed under the skin in close proximity to the primary coil.

Communicating with the processor 768 via communications paths 773 is a transmitter 774 and receiver 776 pair. In this manner, once a physiological parameter of the body is measured, it can be communicated, in a delayed (requires writable memory connected processor 768) or immediate fashion, in a continuous or discrete manner, as processed or raw data, externally to the body so that a practitioner can use the information in treatment of the patient. Preferred transmission methods for the transmitter include, but are not limited to, conduction, radio-frequency waves, magnetic fields, electric fields, sound waves or light waves.

The processor 768 may process various information from its inputs, and may be coupled to a memory storage device (not shown). For example, it may derive systolic and diastolic pressures, mean pressures, heart rate and/or respiratory rate in the event its input included blood pressure waveforms from the pressure input. Once processed, the transceiver could send requests to the processor indicative of how often the blood pressure is to be sampled and which parameters are to be extracted, for example. As another example, the processor could evaluate its ECG input for rhythm disturbances.

In a preferred embodiment, the transceiver 770 includes a second transmitter 775 and receiver 777 pair. It is powered by an appropriate power source 778 such as an AC or DC source. Via communications paths 780, the transmitter 775 and receiver 777 communicate with a second processor 782 having a memory 784. The processor 782 communicates with a visual display 786 so that the practitioner can easily see the value of the measured body physiological parameter. In one embodiment, the display can display more than one physiological parameter at a time. In another, it can cycle between pages of displays. An alarm 788 is provided to aurally and/or visually indicate that one or more of the measured body physiological parameters has exceeded some acceptably defined range of values. In this manner, the patient and/or practitioner can react swiftly in taking corrective action.

An external connector(s) 790 is provided so that the transceiver can become more robust. In various embodiments, the external connector can connect by a direct wire or wireless link, such as by radio-frequency or infrared, to a printer, a general or special purpose computer, additional storage devices, faxes, internet, intranets, cell phone, personal data assistant, satellite, or other such computing or peripheral devices.

It will be appreciated the exact embodiment of the transceiver 770 can embody many forms. For example, in one embodiment it consists of patient strap-on module. In another, it is embodied as a wand to be passed over the patient's skin. In still another, it is coupled physically and electronically together with an infusion pump.

Figure 10A:
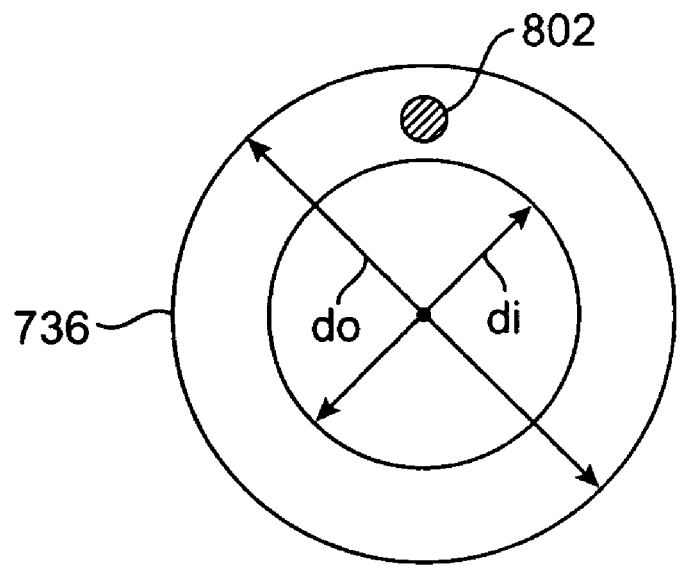
FIG. 10A is an end view of an alternative embodiment of a pressure transmission catheter having an antenna.
Figure 10B:
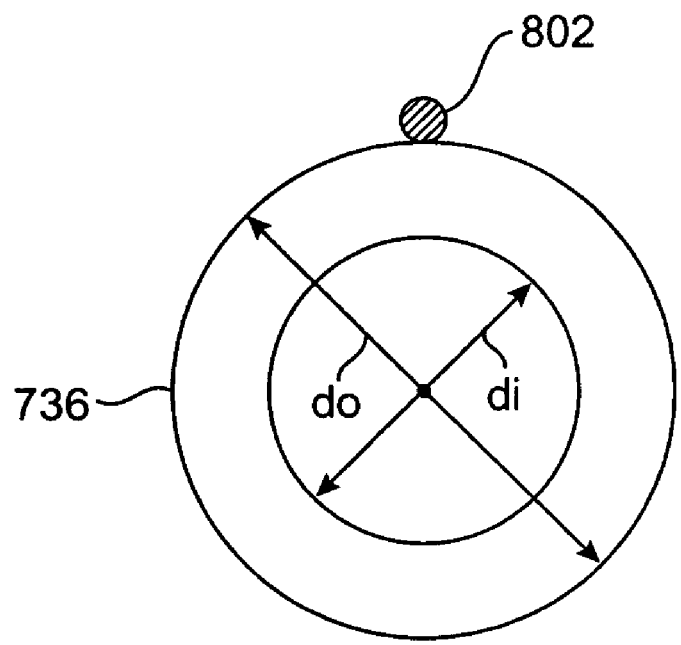
FIG. 10B is an end view of another alternative embodiment of a pressure transmission catheter having an antenna.

The transmitter and receiver pair of the electronics package 760 and the transmitter and receiver pair of the transceiver 770 may communicate via the use of an antenna associated with the PTC 736 or infusion catheter 728. In FIGS. 9A and 9B, and 10A and 10B, an antenna 800 is shown with PTC 736. The catheter may have a length (l), and an inner and outer diameter (di and do). The antenna 800 is disposed along a length thereof in a substantially straight manner (as shown), spirally wound manner, or may consist of a plurality of conductors, stranded or braided, to provide flexibility and ruggedness. A terminal end 802 of the antenna 800 may be disposed in or adjacent the inner diameter (FIG. 9B), adjacent the outer diameter (FIG. 10B), or between the inner and outer diameters (FIG. 10A). In still other embodiments, the antenna is disposed along only a portion of the length of the catheter and a plurality of antennas, instead of just the one shown, are arranged about the inner and outer diameters of the catheter.

The transmitter and receiver pairs may include appropriate modulators, demodulators, amplifiers, oscillators, etc., that are well known and necessary for transmitting and receiving signals, in order to accommodate antenna 800. In some embodiments, it will be appreciated that the electronics package only includes a transmitter for communicating externally to the body and does not include a receiver and therefore cannot receive body external information.

Figure 11A:
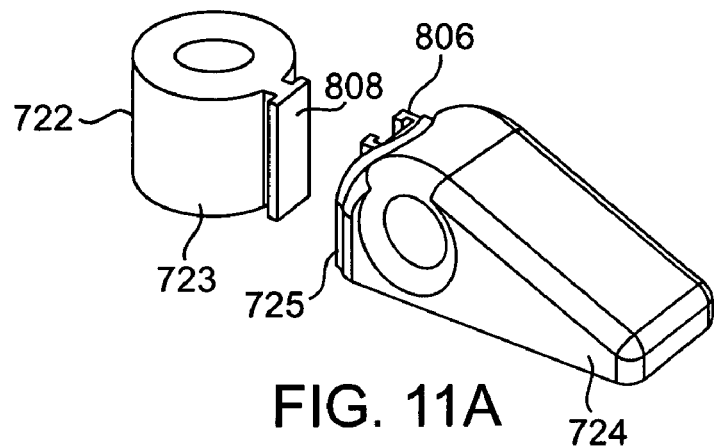
FIG. 11A is a perspective view of a vascular access port and physiological monitoring apparatus having an alternative connector element.
Figure 11B:
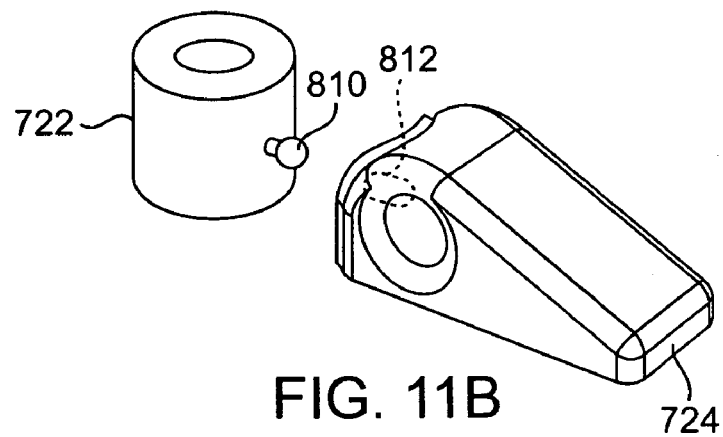
FIG. 11B is a perspective view of a vascular access port and physiological monitoring apparatus having another alternative connector element.
Figure 11C:
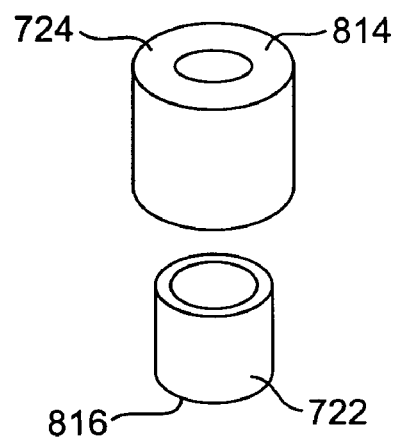
FIG. 11C is a perspective view of a vascular access port and physiological monitoring apparatus connected together by a cooperative geometry.

With reference to FIGS. 11A–11C, it will be appreciated that the VAP and PMA may, instead of being integrally formed, be combinable with one another before, during or after surgical implantation. In such instances, each of the VAP and the PMA have housings having mating, combinable features. For example, in FIG. 11A, the vascular access port housing 722 is slidingly engaged with the PMA housing 724 via mating slot 806 and tab 808 features arranged on an external surface 723, 725 of the VAP and PMA, respectively. In FIG. 11B, the two housings are combinable in an interlocking fit configuration as a ball 810 and socket 812. It will be appreciated that the male/female parts may be switched and are not limited to the embodiments shown. In FIG. 11C, the two housings are combinable as a cap 814 over base 816 configuration. Still other embodiments include, but are not limited to, one-or-more snap-lock features, tongue-groove configurations, or other known or hereinafter invented arrangements. In still other embodiments, the two housings are compatible shapes but are not positively interlocking, such as with a donut shaped PMA surrounding a donut-hole shaped VAP. It should also be appreciated that in any of the foregoing embodiments, more than one PMA may be combined together with a VAP. Also, when made as combinable housings, flexibility is gained because the VAP and PMA can be made and shipped separate from one another and connected in the operating room upon implantation.

Figure 12:
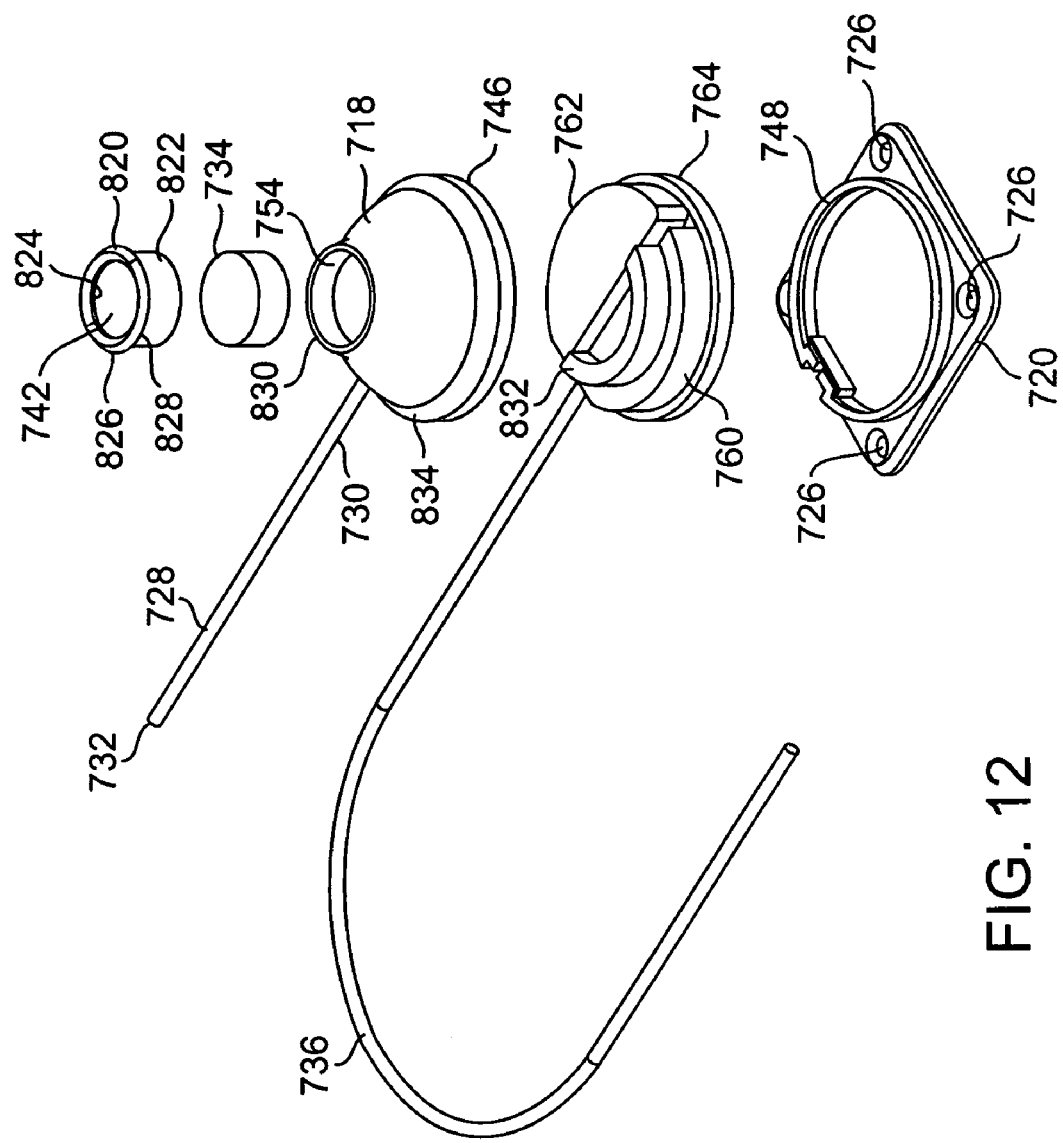
FIG. 12 is an exploded perspective view of an alternative embodiment of a vascular access port and physiological monitoring apparatus connected together by a common or integral housing.

With reference to FIG. 12, another embodiment of a combined VAP and PMA is shown. In this embodiment, the cap 718 defines the fluid reservoir 754 and the mating cap 718 and base 720 pair contain both the VAP and the physiological monitoring device. A bezel 820 secures infusion septum 734 when inner ring 822 is inserted into the fluid reservoir 754. The inner ring is slightly smaller in diameter than the fluid reservoir. An inner lip 824 on the outer ring 826 prevents the infusion septum from slipping out of the bezel. An outer lip 828 abuts a top 830 of the fluid reservoir 754 when the inner ring is inserted therein. An infusion septum access port 742 provides needle access to the infusion septum during use. An infusion catheter 728 is fluidly interconnected to the fluid reservoir at a proximal end 730 for communicating a therapeutic agent from the needle (not shown) to a patient via distal end 732 during use.

An edge 746 of the cap 718 mates about a wall periphery 748 of the base 720 to secure the cap and base together. Located between the cap and base, preferably as a hermetically sealed module, is the electronics package 760, battery source 762, pressure sensor 832 and PTC 736. The electronics package and battery source are hemispherically arranged on a substrate 764 to fit within the outer diameter portion 834 of the cap 718. Suture holes 726 are provided to secure the complete apparatus in a patient during use. An antenna, not shown, may also be included with such structure.

In FIG. 13, the mating cap 718 and base 720 sandwich an electronics package 760, battery source 762 on a substrate 764. As input to the physiological monitoring device, a pair of ECG electrodes 840 are mounted on a bottom surface 841 of the base 720. The ECG electrodes monitor an ECG waveform of the patient during use and are implanted in such a manner to achieve this. Electronic interconnections (not shown) provide communications between the electrodes and the electronics package. The fluid reservoir 754 is defined by the cap 718 and is fluidly interconnected to infusion catheter 728. A PTC 736 is coupled to the cap and to the pressure sensor at proximal end 738.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A surgical method of implanting a vascular access port and a sensor device in a body, comprising:

providing a vascular access port including a portal housing containing an internal reservoir with first and second openings, a self-sealing septum disposed in the first opening, and a first catheter having a proximal end connected to the portal housing, the first catheter defining a lumen extending therethrough in fluid communication with the reservoir via the second opening;

providing a physiological sensor device including a sensor, a sensor housing, the sensor being within the housing, and a second catheter having a proximal end connected to the sensor housing;

surgically forming a subcutaneous pocket through an incision;

introducing the first catheter of the vascular access port into the body;

introducing the second catheter of the sensor device into the body;

connecting the sensor housing to the portal housing after the first and second catheters have been introduced into the body; and surgically closing the incision.

2. The surgical method of claim 1, wherein the sensor device is placed adjacent the vascular access port.

3. The surgical method of claim 1, wherein the sensor housing and the portal housing define cooperative geometries, and wherein the cooperative geometries are placed immediately adjacent each other.

4. The surgical method of claim 1, wherein the sensor housing and the portal housing define interlocking geometries, and wherein the interlocking geometries are interlocked with each other.

5. The surgical method of claim 1, wherein the sensor housing and the portal housing are releasably connected to each other.

6. The surgical method of claim 1, wherein the sensor housing and the portal housing are fixedly connected to each other.

7. The surgical method of claim 1, further comprising:

providing a telemetry unit connected to the sensor device; and placing the telemetry unit in the subcutaneous pocket.

8. The surgical method of claim 1, wherein the portal housing is placed in the subcutaneous pocket.

9. The surgical method of claim 1, wherein the sensor housing is placed in the subcutaneous pocket.

10. A method of treating a patient, comprising:

providing a vascular access port including a portal housing containing an internal reservoir with first and second openings, a self-sealing septum disposed in the first opening, and a catheter connected to the portal housing, the catheter defining a lumen extending therethrough in fluid communication with the reservoir via the second opening;

providing a physiological sensor device including a sensor and a sensor housing the sensor being within the housing, and a second catheter having a proximal end connected to the sensor housing; implanting the vascular access port and the sensor device;

connecting the sensor housing to the portal housing after implanting the vascular access port and the sensor device;

administering a therapeutic agent through the vascular access port;

monitoring the patient for an adverse effect using the sensor device; and transmitting a signal to a caregiver when the adverse effect is detected.

11. The medical treatment method of claim 10, further comprising:

changing the administration of the therapeutic agent as a function of a physiological measure monitored by the sensor device.

12. The medical treatment method of claim 10, further comprising:
providing a telemetry unit connected to the sensor device;
implanting the telemetry unit;
wherein the sensor device generates a sensor signal as a function a physiological measure monitored by the sensor device; and
wherein the telemetry unit generates a transmission signal as a function the sensor signal.

* * * * *